United States Patent [19]

Fujino

[11] Patent Number: 4,490,291

[45] Date of Patent: Dec. 25, 1984

[54] NONAPEPTIDE AMIDES

[75] Inventor: Masahiko Fujino, Hyogo, Japan

[73] Assignee: Takeda Chemical Industries, Ltd., Osaka, Japan

[21] Appl. No.: 596,810

[22] Filed: Jul. 17, 1975

Related U.S. Application Data

[63] Continuation of Ser. No. 491,482, Jul. 24, 1974, abandoned.

[30] Foreign Application Priority Data

Jul. 24, 1973 [JP] Japan ..................................... 83389
Mar. 19, 1974 [JP] Japan ..................................... 31734

[51] Int. Cl.$^3$ ..................... C07C 103/52; A61K 37/00
[52] U.S. Cl. ........................... 260/112.5 LH; 424/177
[58] Field of Search ............... 260/112.5 LH; 424/177

[56] References Cited

PUBLICATIONS

D. H. Coy, et al., Biochem. and Biophys. Res. Comm. 57, 1974, pp. 335–340.

Primary Examiner—Delbert R. Phillips
Attorney, Agent, or Firm—Wenderoth, Lind & Ponack

[57] ABSTRACT

The novel nonapeptide amide derivatives of the formula

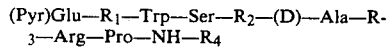

(Pyr)Glu—$R_1$—Trp—Ser—$R_2$—(D)—Ala—$R_3$—Arg—Pro—NH—$R_4$ wherein $R_1$ is His, Tyr, Trp or p-$NH_2$—Phe; $R_2$ is Tyr or Phe; $R_3$ is Leu, Ile or Nle and $R_4$ is alkyl of 1 to 3 carbon atoms which may be substituted with hydroxyl group have a strong ovulation inducing activity.

18 Claims, No Drawings

NONAPEPTIDE AMIDES

This application is a continuation of application Ser. No. 491,482, filed July 24, 1974 (now abandoned).

The present invention relates to novel nonapeptide amide derivatives having strong ovulation inducing activity, which are represented by the formula:

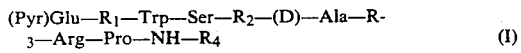

$$\text{(Pyr)Glu—R}_1\text{—Trp—Ser—R}_2\text{—(D)—Ala—R}_3\text{—Arg—Pro—NH—R}_4 \quad \text{(I)}$$

wherein $R_1$ is His, Tyr, Trp or p-NH$_2$—Phe; $R_2$ is Tyr or Phe; $R_3$ is Leu, Ile or Nle and $R_4$ is alkyl of 1 to 3 carbon atoms which may be substituted with hydroxyl group.

The present invention relates also to a method for producing the nonapeptide amide derivatives (I).

In the present specification and the claims, amino acids and peptides are designated by abbreviations which are in common usage in the particular field of art or which have been approved by Committee on Biochemical Nomenclature of IUPAC-IUB. Amino acid is in the L-configuration unless otherwise designated.

The following abbreviations are used, for instance.
Ala: Alanine
Arg: Arginine
BOC: t-Butoxycarbonyl
Bzl: Benzyl
DCC: N,N'-dicyclohexylcarbodiimide
His: Histidine
HONB: N-hydroxy-5-norbornene-2,3-dicarboximide
HOSu: N-hydroxysuccinimide
IBOC: Isobornyloxycarbonyl
Ile: Isoleucine
Leu: Leucine
Nle: Norleucine
OMe: Methyl ester
OBzl: Benzyl ester
ONB: N-hydroxy-5-norbornene-2,3-dicarboxiimide ester
OSu: N-hydroxysuccinimide ester
Phe: Phenylalanine
p.NH$_2$—Phe: p-Aminophenylalanine
Pro: Proline
(Pyr)Glu: Pyroglutamic acid
Ser: Serine
Tos: Tosyl
Trp: Tryptophan
Tyr: Tyrosine
Z: Benzyloxycarbonyl Referring to the above substituent $R^4$, the straight or branched alkyl group of 1 to 3 carbon atoms which may be substituted with hydroxyl group is exemplified by methyl, ethyl, n-propyl, i-propyl, hydroxy-methyl, 1-hydroxyethyl, 2-hydroxyethyl, 2-hydroxy-n-propyl, 3-hydroxy-n-propyl, 2,2-dihydroxy-i-propyl or the like.

It was known for many years that the hypothalamus contains factors which, at a higher level, control the secretion of tropic hormones from the pituitary. Recently, subsequent to the isolation of a thyrotropin-releasing hormone (TRH), a hormone which promotes the secretion of luteinizing hormone has been extracted in pure form from pigs and sheep and shown to be a decapeptide of the structure: H—(Pyr)Glu—His—Trp—Ser—Tyr—Gly—Leu—Arg—Pro—Gly—NH$_2$.
[A. V. Schally et al, Biochem. Biophys. Res. Commun., 43, 1334 (1971): R. Guillemin et al, Proc. Nat. Acad. Sci., U.S.A., 69, 278 (1972)]. This finding has been followed by the synthesis of a number of similar peptides and biological tests have also been performed on these analogous peptides. However, even a minor modification in the above amino acid composition diminishes seriously the physiological activity of the peptide and the above chemical structure has been considered to be essential to the genesis of maximal physiological activity. [A. V. Schally et al, Biochem. Biophys. Res. Commun., 48, 366 (1972)].

Under the circumstances, the present inventor has succeeded in synthesizing nonapeptide amide derivatives (I) and has surprisingly found that these compounds have more potent ovulation inducing activity than the naturally-occurring decapeptide. It has been also found by the present inventor that those compounds act upon the pituitary to promote the secretion of both luteinizing hormone and follicle-stimulating hormone. The present inventor further has found that those compounds are useful not only as drugs for human beings, e.g. drugs for diagnosis of the pituitary function or the gonadotropin deficiency and therapy of amenorrhea, but also as veterinary drugs particularly for the purpose of the animal breeding. The present invention is the culmination of those unexpected findings.

Therefore, it is the main object of the present invention to provide novel nonapeptide amide derivatives (I) which have strong ovulation inducing activity.

Another object of the present invention is to provide a method for the production of the nonapeptide amide derivatives (I).

Further objects of the present invention will be made clear in accordance with the description mentioned hereinafter in this specification.

The nonapeptide amide derivative (I) is produced by a method characterized by that a reagent (A)—L-pyroglutamic acid or a peptide fragment which has a L-pyroglutamic acid unit (i.e. H—(Pyr)Glu—) at its N-terminal end and at the same time which, from thereon, comprises the above amino acid sequence—is condensed with a reagent (B)—an amine component which corresponds to the balance of the nonapeptide amide derivative (I)—, said two reagents (A) and (B) being optionally protected by protecting group or groups, and then the protecting group or groups if any are removed.

Thus, the reagent (A) is L-pyroglutamic acid or a peptide fragment which has an L-pyroglutamic acid unit at its N-terminal end and at the same time which from thereon comprises amino acid sequence of formula (I), and the reagent (B) to be condensed with the reagent (A) is an amine component which corresponds to the balance of the nonapeptide amide derivative (I), the reagents (A) and (B) being optionally protected.

Basic combinations of the reagent (A) and the reagent (B) are exemplified in the following Table 1.

TABLE 1

| Combination | Reagent (A) | Reagent (B) |
|---|---|---|
| 1 | (Pyr)Glu—OH | H—R$_1$—Trp—Ser—R$_2$—(D)-Ala—R$_3$—Arg—Pro—NH—R$_4$ |

TABLE 1-continued

| Combination | Reagent (A) | (B) |
|---|---|---|
| 2 | (Pyr)Glu—$R_1$—OH | H—Trp—Ser—$R_2$—(D)-Ala—$R_3$—Arg—Pro—NH—$R_4$ |
| 3 | (Pyr)Glu—$R_1$—Trp—OH | H—Ser—$R_2$—(D)-Ala—$R_3$—Arg—Pro—NH—$R_4$ |
| 4 | (Pyr)Glu—$R_1$—Trp—Ser—OH | H—$R_2$—(D)-Ala—$R_3$—Arg—Pro—NH—$R_4$ |
| 5 | (Pyr)Glu—$R_1$—Trp—Ser—$R_2$—OH | H—(D)-Ala—$R_3$—Arg—Pro—NH—$R_4$ |
| 6 | (Pyr)Glu—$R_1$—Trp—Ser—$R_2$—(D)-Ala—OH | H—$R_3$—Arg—Pro—NH—$R_4$ |
| 7 | (Pyr)Glu—$R_1$—Trp—Ser—$R_2$—(D)-Ala—$R_3$—OH | H—Arg—Pro—NH—$R_4$ |
| 8 | (Pyr)Glu—$R_1$—Trp—Ser—$R_2$—(D)-Ala—$R_3$—Arg—OH | H—Pro—NH—$R_4$ |
| 9 | (Pyr)Glu—$R_1$—Trp—Ser—$R_2$—(D)-Ala—$R_3$—Arg—Pro—OH | $NH_2$—$R_4$ |

It has also been known that a protected L-glutamyl group shown by the general formula (II):

$$RCO—CH_2CH_2CH(NH_2)CO— \quad (II)$$

[wherein R is an alkoxy group (e.g. methoxy, ethoxy, n-propoxy, i-propoxy, n-butoxy, etc.), an aralkyloxy group (e.g. benzyloxy, etc.) or amino] is easily converted to the L-pyroglutamyl group itself:

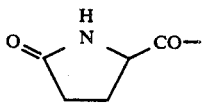

by the contact with a base (e.g. ammonia, etc.) or an acid (e.g. acetic acid etc.) and that the group (II) is equivalent to L-pyroglutamyl group itself in this respect. In the method of the present invention, it is to be construed that the L-pyroglutamyl (i.e. H—(Pyr)-Glu—) of the reagent (A) includes not only the L-pyroglutamyl group itself but also the protected L-glutamyl group of the formula (II). In case when H—(Pyr)Glu— of the reagent (A) represents the group (II), the group (II) is easily converted to L-pyroglutamyl group itself in accordance with per se known means.

The condensation reaction according to this invention can be carried out by condensing means known for the formation of peptide linkages. Among such means of condensation are the azide process, chloride process, acid anhydride process, mixed acid anhydride process, DCC process, active ester process, Woodward reagent K process, carbodiimidazole process, oxidation-reduction process, DCC/HONB process and others [The Peptides, Vol. 1 (1966), Schröder and Lubke, Academic Press, New York, U.S.A. and Belgian Pat. No. 796,399].

Prior to the condensation reaction, one may protect the carboxyl and amino groups which should not be involved in the contemplated reaction or activate the carboxyl or/and amino groups which will take part in the reaction, by means which are known per se. The carboxyl groups in the starting material may be protected in the form of metal salts (e.g. sodium and potassium salts) or esters (e.g. methyl, ethyl, benzyl, p-nitrobenzyl, t-butyl or t-amyl esters).

Protective groups for amino groups in the starting materials may be any of conventional protecting groups of amino groups in peptide synthesis, e.g. benzyloxycarbonyl, t-butoxycarbonyl, isobornyloxycarbonyl, etc. The hydroxyl group of serine may be protected with a conventional protective group such as benzyl, t-butyl and other ether-forming groups. The hydroxyl group of tyrosine may be protected with benzyl, t-butyl and other ether-forming groups; the guanidino group of arginine may be protected with such groups as nitro, tosyl, carbobenzoxy, isobornyloxycarbonyl or adamantyloxycarbonyl. As examples of activated carboxyl groups in starting materials, there may be mentioned the corresponding acid anhydride, azide, active esters [esters with alcohols (e.g. pentachlorophenol, 2,4,5-trichlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide or N-hydroxybenztriazole], etc. The activated amino groups in starting materials may for example be the corresponding phosphoric acid amide.

The following table shows some exemplary combinations of such forms of carboxyl and amino groups in materials (A) and (B).

TABLE 2

| Exemplary combinations | Reagents (A) | | (B) | |
|---|---|---|---|---|
|  | COOH | $NH_2$ | COOH | $NH_2$ |
| 1* | Free | Protected | Protected | Free |
| 2 | Activated | Protected | Free | Free |
| 3 | Free | Protected | Protected | Activated |

(Note)
In the case designated by an asterisk *, a dehydrating agent (e.g. a carbodiimide reagent such as dicyclohexyl-carbodiimide) is preferably present in the reaction system. A mode of practice of this invention may be written as follows.

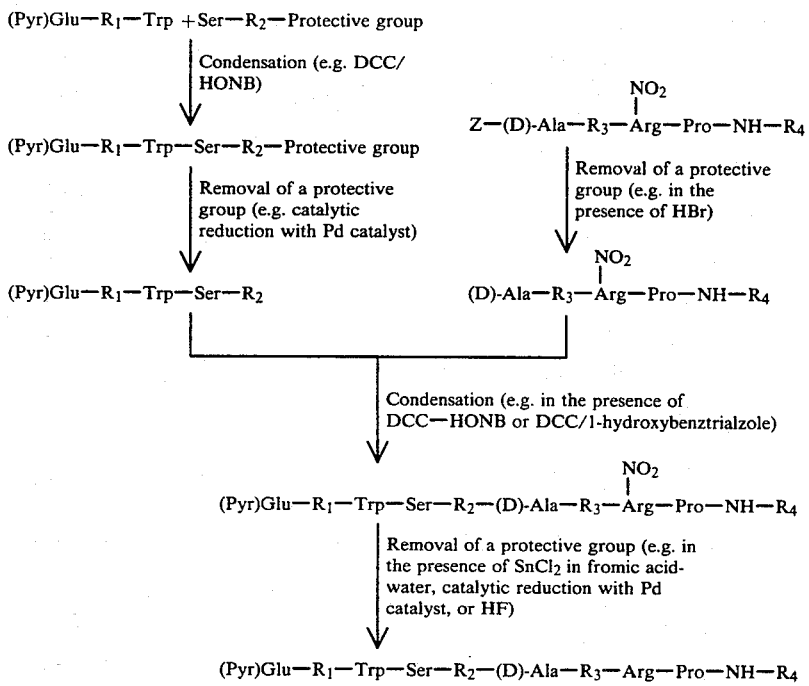

This reaction may be conducted in the presence of a solvent. The solvent can be selected from those known to be useful for peptide condensation reactions. Thus, anhydrous or aqueous dimethylformamide, dimethylsulfoxide, pyridine, chloroform, dioxane, dichloromethane, tetrahydrofuran and suitable mixtures of such solvents may be mentioned by way of example.

The reaction temperature is selected from within the range known to be employable for reactions leading to the formation of peptide bonds, i.e. normally within the range of about $-20°$ C. to about $30°$ C. Further, the precursor materials (protected peptides) of the contemplated compounds according to this invention may also be easily prepared by solid-phase synthetic processes.

After the contemplated condensation reaction has been completed, if the product carries protective groups, they can be removed by routine procedures. Among such routine procedures are catalytic reduction in the presence of a catalyst such as palladium black, palladium-on-carbon, platinum or the like, hydrolysis by means of hydrogen fluoride, trifluoroacetic acid or the like, and reduction with metallic sodium in liquid ammonia.

The peptide (I) thus produced can be recovered from the reaction product mixture by procedures known for the recovery of peptides, e.g. by extraction, distribution, column chromatography, etc.

The peptide (I) may also be recovered in the form of a salt or metal complex compound.

As acids which are able to form salts with peptide (I), there may be mentioned inorganic acids such as hydrochloric acid, hydrobromic acid, perchloric acid, nitric acid, thiocyanic acid, sulfuric acid, phosphoric acid, etc. and organic acids such as formic acid, acetic acid, propionic acid, glycolic acid, lactic acid, pyruvic acid, oxalic acid, malonic acid, succinic acid, maleic acid, fumaric acid, anthranylic acid, cinnamic acid, naphthalenesulfonic acid or sulfanylic acid, for instance.

The metals which are able to form metal complex compounds with peptide (I) include, among others, zinc, nickel, cobalt, copper and iron. Such a metal complex compound can be produced by conventional procedures, for example, by reacting peptide (I) with the hydroxide or oxide of a metal of the above-mentioned variety at pH about 6 to 8.

The polypeptides (I) according to this invention have LH-RH (luteinizing hormone releasing hormone) activity and, accordingly, are able to promote the secretion of LH (luteinizing hormone) and FSH (follicle stimulating hormone). Therefore, polypeptides (I) are of use as drugs for promoting ovulations in women and other animals (e.g. rats, ewes, pigs, cows, mares, quails or hens). The peptides can also be used for other pharmaceutical purposes for which conventional LH-RH, LH and FSH preparations have been employed.

Since the LH-RH activity of polypeptides (I) is about 20 times that of known naturally-occurring LH-RH, their dosage may be determined for each application on the basis of the above multiple whilst other factors (e.g. the subject of administration of the kind of disease) are also taken into consideration. For example, a suitable dosage may be selected from within the range of about 2 ng. to 2 $\mu$g. daily per kilogram of body weight.

Polypeptides (I) are primarily administered nonorally (e.g. by injection or by the rectal or vaginal route), although they are orally administered in certain instances.

The dosage forms employable include, for example, injections, suppositories, pessaries and powders. The injections can be prepared by dissolving about 10$\gamma$ to 100$\gamma$ of polypeptide (I) in 1 ml. of physiological saline. Polypeptides (I) can be also made into lyophilized ampoule products with mannitol added as an excipient so that one may adminster them as injections for extemporaneous use.

The starting material peptides employable in the method of this invention can be prepared either by known processes for peptide synthesis or by utilizing such processes as found necessary.

RELATIVE OVULATION-INDUCING ACTIVITY OF THE PEPTIDE (I)

Ovulation-inducing activity is determined in Sprague-Dawley rats (4-day cycling female) in which the injection of the compound was made subcutaneously at 14:30 on the day of diestrous, and the ovulated ova in the ampilla of the oviduct were examined on the morning of the next day. The results ($ED_{50}$) were compared with that ($ED_{50}$) of LH-RH itself. The assay results on the object compounds are as follows.

| Control | (Pyr)Glu—His—Trp—Ser—Tyr—Gly—Leu—Arg—Pro—Gly—NH$_2$ (natural LH—RH) | | | | 100% |
|---------|------|------|------|-------------|--------|
|         | $R_1$ | $R_2$ | $R_3$ | $R_4$ |        |
| Peptide (I) | His | Tyr | Leu | ethyl | 6,100% |
|         | His | Tyr | Leu | n-propyl | 4,800% |
|         | His | Tyr | Leu | 2-hydroxy-ethyl | 4,300% |
|         | His | Tyr | Leu | iso-propyl | 3,600% |
|         | His | Phe | Leu | ethyl | 5,810% |
|         | His | Phe | Leu | n-propyl | 2,900% |
|         | His | Tyr | Nle | ethyl | 4,800% |
|         | His | Phe | Ile | ethyl | 3,200% |
|         | Tyr | Tyr | Leu | ethyl | 2,010% |
|         | p-NH$_2$—Phe | Tyr | Leu | ethyl | 2,150% |

For further illustration of the invention, examples are given as follows:

In those examples, the following abbreviations mean Rf value of a thin layer chromatography on silica gel with the following solvent system:

Rf$^1$: ethyl acetate:pyridine:acetic acid:water=60:20:6:10
Rf$^2$: n-butanol:ethyl acetate:acetic acid:water=1:1:1:1
Rf$^3$: n-butanol:acetic acid:water=4:1:1
Rf$^4$: chloroform:methanol:acetic acid=9:1:0.5

Explanations of the registered trade names used in the Examples are as follows:

Celite: Filter aid manufactured by Johns-Manville, U.S.A.
Biogel P-2: Materials for gel filtration manufactured by BIO.RAD, U.S.A.
Cephadex LH-20: Esterified dextran gel manufactured by Pharmacia Fine Chemicals, Sweden
Amberlite XAD-2: Polystyrene resin
Amberlite IRA-410: Strongly basic anion exchange resin
Amberlite CG-410: Strongly basic anion exchange resin
Amberlite CG-45: Weakly basic anion exchange resin
All these resins are manufactured by Rohm & Haas Co. Ltd. U.S.A.

EXAMPLE 1

Production of (Pyr)Glu—His—Trp—Ser—Tyr—(D-)—Ala—Leu—Arg—Pro—NH—CH$_2$—CH$_3$ (a) Preparation of (Pyr)—Glu—His—Trp—Ser—Tyr—OH In 100 ml. of methanol is dissolved 8.0 g. of Z—Ser—Tyr—OMe, and with the addition of 500 mg. of palladium black, catalytic reduction is performed at atmospheric temperature and pressure by introducing hydrogen gas in the solution of 4 hours. The catalyst is removed by filtration. The methanol is distilled off under reduced pressure at low temperature and the residue is dissolved in 30 ml. of dimethylformamide. To the solution are added 6.78 g. of crystals of (Pyr)-Glu—His—Trp—OH, followed by cooling with ice. Thereafter, 5.4 g. of HONB and 5.0 g. of DCC are added and the entire mixture is stirred on an ice-bath for 8 hours and at room temperature for 10 hours.

The resultant byproduct dicyclohexylurea is filtered off and the filtrate is concentrated under reduced pressure. Following the addition of 100 ml. of ether, the precipitate formed is recovered by filtration, washed with ether and dried. Yield 12.2 g. This product is dissolved in a mixture of ethyl acetate-pyridine-acetic acid-water (60:20:6:10).

The solution is run onto a column (6.5 cm diameter×19 cm) of silica gel prepared with the same solvent mixture and the column is eluted with the same solvent mixture, whereupon contemplated (Pyr)Glu—His—Trp—Ser—Tyr—OMe emerges in the 1480 ml. to 1800 ml. fractions. This eluate is concentrated to dryness under reduced pressure and washed well with water. Yield 8.3 g. In thin-layer chromatography on silica gel, this product gives a single Pauly and Ehrlich-positive spot each at Rf$^1$=0.29, Rf$^2$=0.68, and Rf$^3$=0.43.

In 50 ml. of methanol is dissolved 7.2 g. of this product and, under cooling with ice, 30 ml. of 1N sodium hydroxide is slowly added to effect hydrolysis. The solution is stirred at room temperature for 3 hours. Then, following the addition of 30 ml. of 1N hydrochloric acid, the solution is cooled, whereupon a precipitate is formed. It is recovered by filtration, washed with cold water and dried. The product is dissolved in 5% aqueous ethanol and the solution is run onto a column (3 cm in diameter×25 cm) of Amberlite XAD-2. Elution is performed by the gradient method using 5% ethanol (800 ml.) and 90% ethanol (800 ml.). Fractions of the desired compound are pooled, concentrated under reduced pressure to remove the ethanol, and lyophilized. Yield 5.9 g. Rf$^1$=0.01, Rf$^2$=0.62, Rf$^3$=0.34.

Elemental analysis (for $C_{34}H_{38}N_8O_9 \cdot H_2O$): Calcd.: C, 56.65; H, 5.59; N, 15.55. Found: C, 56.39; H, 5.70; N, 15.52.

Amino acid analysis (hydrolysis with 5.7N hydrochloric acid in the presence of thioglycolic acid): Glu, 1.05; His, 0.98; Trp, 0.95; Ser, 0.98; Tyr, 1.03

(b) Preparation of Z—(D)—Ala—Leu—Arg(NO$_2$)—Pro—NH—CH$_2$—CH$_3$

In a mixture of 30 ml. of dioxane and 10 ml. of dimethylformamide, there are dissolved 1.14 g. of H—Leu—Arg(NO$_2$)—Pro—NH—CH$_2$—CH$_3$ and 447 mg. of Z—(D)—Ala—OH. To the solution is added 400 mg. of HONB and the mixture is cooled rapidly. Following the addition of 460 mg. of DCC, the mixture is stirred for 20 hours. The resultant by-product dicyclohexylurea is filtered off and the filtrate is concentrated to dryness under reduced pressure. The residue is dissolved in ethyl acetate under warming and the solution is washed with a 4% aqueous solution of sodium bicarbonate and, then, with water, followed by drying over anhydrous sodium sulfate and concentration to dryness under reduced pressure.

The residue is dissolved again in a small amount of ethyl acetate under heating and the solution is filtered to remove the small amounts of insolubles. The filtrate is allowed to stand, whereupon needles separate. These crystals are recovered by filtration, washed with ethyl acetate and dried. Yield 1.30 g. Melting point: 183°–184° C.;

$[α]_D^{26} = -49.2°$ (c=0.5, methanol).

Elemental analysis, for $C_{30}H_{47}O_8N_9$: Calcd.: C, 54.45; H, 7.16; N, 19.05. Found: C, 54.42; H, 7.28; N, 18.86. $Rf^1 = 0.78$, $Rf^2 = 0.90$, $Rf^4 = 0.65$.

(c) Preparation of (Pyr)Glu—His—Trp—Ser—Tyr—(D-)—Ala—Leu—Arg—Pro—NH—CH$_2$—CH$_3$ In 20 ml. of acetic acid are dissolved 155 mg. of crystals of Z—(D)—Ala—Leu—Arg(NO$_2$)—Pro—NH—CH$_2$—CH$_3$ and, following the addition of 100 mg. of palladium black, catalytic reduction is carried out at atmospheric temperature and pressure for 5 hours. The catalyst is filtered off, and following the addition of 0.45 ml. of 1N hydrochloric acid, the filtrate is concentrated to dryness under reduced pressure. The residue is dissolved in 10 ml. of water and lyophilized. The residual white fluffy product and 141 mg. of (Pyr)-Glu—His—Trp—Ser—Tyr—OH are dissolved in 10 ml. of dimethylformamide, followed by the addition of 60 mg. of HONB. Under cooling with ice, 0.25 ml, of a 10% solution of N-ethyl-morpholine in dimethylformamide and, 50 mg. of DCC are added in this order. The mixture is stirred under cooling with ice for 5 hours and, then, at room temperature for 10 hours. The dimethylformamide is distilled off under reduced pressure and 20 ml. of water is added. The insolubles are filtered off and the filtrate is run onto a column (1 cm diameter×5 cm) of Amberlite IRA-410 (acetate form), which is then washed with 50 ml. of water. The effluent and washings are pooled and run onto a column (1.5 cm diameter×25 cm) of carboxymethyl-cellulose. Elution is carried out by the gradient method using 0.005M ammonium acetate (300 ml.) and 0.175M ammonium acetate (300 ml.). The 170 ml.- to 240 ml.-fractions are pooled and lyophilized, whereupon 208 mg. of white fluffy powder is obtained. Thin layer chromatography of this product shows evidence of an impurity having a large Rf value. Therefore, it is further purified by means of a column (2 cm diameter×20 cm) of Amberlite XAD-2. Thus, an aqueous solution of the above fluffy product is run onto a column of Amberlite XAD-2 prepared with water and elution is performed by the gradient method using water (250 ml.) and 75% ethanol (280 ml.). The 170 ml.- to 250 ml.-fractions are pooled and, after removal of the ethanol by distillation under reduced pressure, lyophilized. Yield 129 mg. $Rf^1 = 0.062$; $Rf^2 = 0.358$.

$[α]_D^{26} = 47.0°$ (c=0.5, 5% aqueous solution of acetic acid). Amino acid analysis (hydrolysis with HCl in thioglycolic acid): Glu, 0.98; His, 1.05; Trp, 1.04; Ser, 0.97; Tyr, 0.97; Ala, 1.00; Lue, 1.04; Arg, 1.03; Pro, 1.00; ethylamine, 1.02 (86% recovery).

Similarly, a polypeptide-amide of formula (Pyr)-Glu—His—Trp—Ser—Tyr—(D)—Ala—Leu—Arg—Pro—NHCH$_3$ is obtained using, as one of the starting materials, Z—(D)—Ala—Leu—Arg(NO$_2$)—Pro—NH—CH$_3$ instead of Z—(D)—Ala—Leu—Arg(NO$_2$)—Pro—NH—CH$_2$—CH$_3$ in the above (b). This product has the following physical and chemical properties.

$[α]_D^{24} = -48.1°$ (c=0.6, 5% acetic acid). $Rf^1 = 0.055$; $Rf^2 = 0.335$.

Amino acid analysis (hydrolysis with HCl in the presence of thioglycolic acid); Glu, 1.00; His, 1.02; Trp, 0.89; Ser, 0.90; Tyr, 0.98; Ala, 1.00; Lue, 1.00; Arg, 1.04; Pro, 1.02; methylamine, 0.97 (84.0% recovery).

EXAMPLE 2

Production of (Pyr)Glu—His—Trp—Ser—Tyr(D)—Ala—Leu—Arg—Pro—NH—CH$_2$—CH$_2$—CH$_3$ (a) Preparation of Z—(D)—Ala—Leu—Arg(NO$_2$)—Pro—NH—CH$_2$—CH$_2$—CH$_3$ In 2 ml. of 25% solution of hydrogen bromide in glacial acetic acid is dissolved 720 mg. of Z—Leu—Arg(NO$_2$)—Pro—NH—CH$_2$—CH$_2$—CH$_3$. The solution is shaken for 40 minutes, after which 20 ml. of dry ether is added. The resultant precipitate is recovered by filtration and washed with dry ether. The powder thus obtained is dried under reduced pressure over sodium hydroxide in a desiccator. The dried powder is dissolved in 5 ml. of dimethylformamide and, following the addition of 230 mg. of Z—(D)—Ala—OH and 200 mg. of HONB, the solution is cooled with ice and 1.5 ml. of a 10% solution of triethylamine in dimethylformamide is added. To this solution is added 230 mg. of DCC and the mixture is stirred at room temperature for 10 hours. Most of the dimethylformamide is distilled off under reduced pressure and the residue is dissolved by the addition of 50 ml. of ethyl acetate. The insolubles are filtered off and the filtrate is washed with a 4% aqueous solution of sodium bicarbonate three times and, then, with water twice. The solution is dried over anhydrous sodium sulfate and the ethyl acetate is distilled off. The residue is added to ether and the resultant powder is recovered by filtration.

It is dissolved in ethyl acetate under heating and purified by reprecipitation with ether.

The described procedure yields 723 mg. of powder. $[α]_D^{25} = -48.0°$ (c=1.0, methanol).

Elemental analysis, for $C_{31}H_{48}O_8N_9$: Calcd.: C, 55.18; H, 7.17; N, 18.68. Found: C, 54.89; H, 7.32; N, 18.44. $Rf^4 = 0.62$.

(b) Preparation of (Pyr)Glu—His—Trp—Ser—Tyr—(D-)—Ala—Leu—Arg—Pro—NH—CH$_2$—CH$_2$—CH$_3$ In a mixture of 10 ml. of acetic acid and 10 ml. of methanol, 150 mg. of the Z—(D)—Ala—Leu—Arg-(NO$_2$)—Pro—NH—CH$_2$—CH$_2$—CH$_3$ obtained according to the above (a) is catalytically reduced using palladium-on-carbon as the catalyst for 4 hours. The catalyst is filtered off and the solvent is distilled off from the filtrate under reduced pressure. The residue is dissolved in 0.4 ml. of a mixture of 1N hydrochloric acid and 10 ml. of water, and the solution is lyophilized. The procedure gives white fluffy powders.

This product and 141 mg. of (Pyr)Glu—His—Trp—Ser—Tyr—OH are dissolved in 10 ml. of dimethylformamide, followed by the addition of 60 mg. of HONB and 0.25 ml. of a 10% solution of N-ethylmorpholine in dimethylformamide. The mixture is cooled to $-2°$ C. and 55 mg. of DCC is added. The mixture is stirred under cooling with ice for 5 hours and, then, at room temperature for 12 hours.

After the reaction has been completed, the dimethylformamide is distilled off under reduced pressure and the residue is dissolved in 20 ml. of water. The small amount of insolubles (dicyclohexyl-urea) is filtered off and the filtrate is run onto a column (1 cm diameter×4 cm) of Amberlite IRA-410 (acetate form), which is then washed with water. The effluent and washings are pooled and run onto a column (1.5 cm diameter×25 cm) of carboxymethylcellulose.

After washing with 0.005M ammonium acetate buffer, continuous elution is carried out using 300 ml. of 0.005M ammonium acetate buffer (pH 6.8) and 300 ml. of 0.2M ammonium acetate buffer (pH 6.9). The 160 ml.- to 230 ml.-fractions are pooled, lyophilized, re-chromatographed under the same conditions as above, and lyophilized for a second time. The product is applied to a column (3 cm diameter×50 cm of Biogel P-2 (5% acetic acid as eluant) and the eluate containing the desired product is lyophilized. The described procedure gives 201 mg. of white fluffy powder.

$[\alpha]_D^{25} = -46.8°$ (c=0.5, 5% acetic acid).
$Rf^2 = 0.37$; $Rf^1 = 0.08$.

Amino acid analysis (hydrolysis with 5.7N hydrochloric acid in the presence of thioglycolic acid): His, 0.97; Arg, 0.97; Trp, 0.91; Ser, 0.91; Glu, 1.00; Pro, 1.00; Ala, 0.98; Lue, 0.97; Tyr, 0.94 (86.4% recovery.)

EXAMPLE 3

Production of
(Pyr)Glu—His—Trp—Ser—Tyr—(D-)—Ala—Leu—Arg—Pro—NH—CH$_2$—CH$_2$—OH (a) Preparation of
Z—(D)—Ala—Leu—Arg(NO$_2$)—Pro—NH—CH$_2$—CH$_2$—OH In 3 ml. of 20% solution of hydrogen bromide in dioxane is dissolved 722 mg. of Z—Leu—Arg(NO$_2$)—Pro—NH—CH$_2$—CH$_2$—OH. The solution is shaken for 60 minutes, after which 30 ml. of dry ether is added. The precipitate is recovered by decantation, washed with dry ether and dried well over sodium hydroxide in a desiccator under reduced pressure.

The product is dissolved in 5 ml. of dimethylformamide, followed by the addition of 230 mg. of Z—(D-)—Ala—OH and 210 mg. of HONB. After cooling with ice, 0.16 ml. of triethylamine and, 230 mg. of DCC are added in this order. The mixture is stirred under cooling with ice for 1 hour and, then, at room temperature for 4 hours. The reaction mixture is filtered and the filtrate is added to 100 ml. of chloroform. The solution is washed with a 4% aqueous solution of sodium bicarbonate and, then, with water, dried over anhydrous sodium sulfate and concentrated to dryness under reduced pressure. The residue is dissolved in a solvent mixture of chloroform, methanol and acetic acid (9:1:0.5) and the solution is run onto a column (3 cm diameter×40 cm) of silica gel prepared with the same kind of the solvent as above, followed by development with the same kind of the solvent. The fractions giving an Rf$^4$ value of 0.47 are pooled, concentrated to dryness under reduced pressure and washed with ether. The described procedure gives 640 mg. of powders.

$[\alpha]_D^{26} = -47.2°$ (c=0.5, methanol).

Elemental analysis, for C$_{30}$H$_{47}$O$_9$N$_9$: Calcd.: C, 53.16; H, 6.99; N, 18.60. Found: C, 52.84; H, 7.26; N, 18.21.
$Rf^4 = 0.47$.

(b) Preparation of
(Pyr)Glu—His—Trp—Ser—Tyr—(D-)—Ala—Leu—Arg—Pro—NH—CH$_2$—CH$_2$—OH In 10 ml. of acetic acid, 154 mg. of the Z—(D-)—Ala—Leu—Arg(NO$_2$)—Pro—NH—CH$_2$—CH$_2$—OH is catalytically reduced using palladium black as the catalyst for 5 hours. The catalyst is filtered off and the filtrate is concentrated to dryness under reduced pressure. Following the addition of 10 ml. of water and 0.45 ml. of 1N hydrochloric acid, the concentrate is lyophilized. The powdery lyophilizate and 140 mg. of (Pyr)Glu—His—Trp—Ser—Tyr—OH are dissolved in 10 ml. of dimethylformamide, followed by the addition of 60 mg. of HONB and 0.25 ml. of a 10% solution of N-ethylmorpholine in dimethylformamide. The mixture is cooled to $-2°$ C. and 60 mg. of DCC is added. The mixture is stirred under cooling with ice for 6 hours and, then, at room temperature for 12 hours. After the reaction has gone to completion, the dimethylformamide is distilled off under reduced pressure and the residue is dissolved in 10 ml. of water. The insolubles are filtered off and the filtrate is passed through a column (1 cm diameter×4 cm) of Amberlite IRA-410 (acetate form), whereby the product is converted to the acetate. Thereafter, the salt is purified by means of a column of carboxymethyl-cellulose and a column of Amberlite XAD-2 in the same manner as Example 1. After lyophilization, there are obtained white fluffy powder. Yield 146 mg.

$[\alpha]_D^{25} = -48.1°$ (c=0.5, 5% acetic acid).
$Rf^2 = 0.31$, $Rf^1 = 0.025$.

Amino acid analysis (hydrolysis with 5.7N hydrochloric acid in the presence of thioglycolic acid): His, 1.00; Arg, 0.98; Trp, 0.98; Ser, 0.92; Glu, 1.00; Pro, 1.00; Ala, 0.99; Leu, 1.00; Tyr, 0.98 (87% recovery).

EXAMPLE 4

Production of
(Pyr)Glu—His—Trp—Ser—Tyr—(D-)—Ala—Leu—Arg—Pro—NH—CH(CH$_3$)$_2$ (a) Preparation of
Z—(D)—Ala—Leu—Arg(NO$_2$)—Pro—NH—CH(CH$_3$)$_2$ 720 mg. of Z—Leu—Arg(NO$_2$)—Pro—NH—CH(CH$_3$)$_2$ is treated in the same manner as Example 2-(a) and, then, condensed with Z—(D)—Ala—OH in a mixture of 5 ml. of dimethylformamide and 10 ml. of dichloromethane with the aid of DCC and HONB. The product is extracted with ethyl acetate to obtain 690 mg. of powders.

$[\alpha]_D^{25} = -48.3°$ (c=1.0, methanol).

Elemental analysis, for C$_{31}$H$_{48}$O$_8$N$_9$: Calcd.: C, 55.18; H, 7.17; N, 18.68. Found: C, 54.78; H, 7.09; N, 18.22.
$Rf^4 = 0.61$.

(b) Preparation of
(Pyr)Glu—His—Trp—Ser—Tyr—(D-)—Ala—Leu—Arg—Pro—NH—CH(CH$_3$)$_2$ By exactly the same procedure as that described in Example 2-(b), the above compound is prepared from Z—(D)—Ala—Leu—Arg(NO$_2$)—Pro—NH—CH(CH$_3$)$_2$ and (Pyr)Glu—His—Trp—Ser—Tyr—OH. Yield 128 mg.

$[\alpha]_D^{25} = -47.5°$ (c=0.5, 5% acetic acid).
$Rf^2 = 0.375$, $Rf^1 = 0.08$.

Amino acid analysis (hydrolysis with 5.7N hydrochloric acid in the presence of thioglycolic acid): His, 0.99; Arg, 0.98; Trp, 0.89; Ser, 0.94; Glu, 1.00; Pro, 1.00; Ala, 1.00; Leu, 1.02; Tyr, 0.98 (86.5% recovery)

EXAMPLE 5

Production of (Pyr)Glu—His—Trp—Ser—Phe—(D-)—Ala—Leu—Arg—Pro—NH—CH$_2$—CH$_3$ (a) Preparation of (Pyr)Glu—His—Trp—Ser—Phe—OH In 100 ml. of methanol are dissolved 4.0 g. of Z—Ser—Phe—OMe. The solution is subjected to a catalytic reduction with 500 mg. of palladium black at atmospheric pressure for 1.5 hours. The catalyst is removed by filtration and immediately the methanol is evaporated from the filtrate by distillation under reduced pressure and the residue is dissolved in 25 ml. of dimethylformamide. To the solution is added 4.1 g. of (Pyr)Glu—His—Trp—OH, followed by the addition of 3.8 g. of HONB and 3 g. of DCC at −5° C. The mixture is stirred at −5° C. for 2 hours, at 0° C. for 2 hours and at room temperature for 8 hours.

The resultant dicyclohexylurea is removed by filtration and the filtrate is concentrated to dryness under reduced pressure. The residue is triturated with ethyl acetate and the resultant powder is collected by filtration. Yield: 6.7 g. The powder is dissolved in 30 ml. of a mixture of methanol and chloroform (15:85) and the solution is run onto a column (6 cm diameter × 12 cm) of silica gel prepared with a mixture of methanol and chloroform (15:85). The column is eluted with 600 ml. of a mixture of methanol and chloroform (15:85), 1 l. of a mixture of methanol and chloroform (25:75) and 1 l. of a mixture of methanol and chloroform (30:70). Fractions which is eluted with from 400 ml. of the mixture of methanol and chloroform (25:75) to 700 ml. of the mixture of methanol and chloroform (30:70) are pooled and concentrated to dryness under reduced pressure. The residue is triturated with ethyl acetate and the resultant powder is recovered by filtration to yield the compound [(Pyr)Glu—His—Trp—Ser—Phe—OMe]. Yield: 4.2 g. Rf$^1$=0.29.

In 20 ml. of methanol is suspended 3.5 g. of the compound which is produced just above and the suspension is cooled to 0° C., followed by the addition of 8 ml. of N sodium hydroxide solution. The mixture is stirred for one hour and neutralized with 8 ml. of N hydrochloric acid. The methanol is distilled off under reduced pressure and cold water is added to the residue. The resultant precipitates are collected by filtration, washed with cold water and dried to yield the object compound. Rf$^2$=0.61.

$[\alpha]_D^{26.5}$ = −3.3° (c=0.55, glacial acetic acid).

(b) Production of (Pyr)Glu—His—Trp—Ser—Phe—(D-)—Ala—Leu—Arg(NO$_2$)—Pro—NH—CH$_2$CH$_3$ In 15 ml. of 25% solution of hydrogen bromide in glacial acetic acid is dissolved 1.6 g. of Z—(D-)—Ala—Leu—Arg(NO$_2$)—Pro—NH—CH$_2$CH$_3$ and the solution is stirred at room temperature for 50 minutes. To the solution is added 150 ml. of dry ether and the resultant precipitates are collected by filtration, dried and dissolved in 30 ml. of water. The solution is run onto a column (2.5 cm diameter × 15 cm) of Amberlite CG-410 (free base) and the column is washed well with a mixture of methanol and water (30:70). The effluent and the washing are combined and concentrated to evaporate the methanol. The residue is lyophilized to yield H—(D)—Ala—Leu—Arg(NO$_2$)—Pro—NHCH$_2$CH$_3$. Yield 1.2 g. Rf$^1$=0.21, Rf$^2$=0.64.

In 5 ml. of dimethylformamide are dissolved 225 mg. of the compound which is produced just above and 280 mg. of (Pyr)Glu—His—Trp—Ser—Phe—OH, followed by the addition of 150 mg. of HONB. The mixture is cooled to −10° C. and 90 mg. of DCC is added. The mixture is stirred at −10° C. for 2 hours, at 0° C. for 4 hours and at room temperature for 12 hours. The resultant mixture is filtered to remove the dicyclohexylurea and ethyl acetate is added to the filtrate. The resultant precipitates are collected by filtration, dried and dissolved in a mixture of ethanol and water (20:80) under heating. The solution is left standing to yield fine crystals and the crystals are collected by filtration. Yield 389 mg.

$[\alpha]_D^{26.5}$ = −43.6° (c=0.11, methanol) Rf$^1$=0.22, Rf$^2$=0.74.

(c) Production of (Pyr)Glu—His—Trp—Ser—Phe—(D-)—Ala—Leu—Arg—Pro—NH—CH$_2$CH$_3$ (I) In 10 ml. of 60% aqueous solution of formic acid is dissolved 150 mg. of the compound [H—(D-)—Ala—Leu—Arg(NO$_2$)—Pro—NH—CH$_2$CH$_3$] which is produced as in the above (b), followed by the addition of 300 mg. of SnCl$_2$.H$_2$O. The mixture is heated at 80° to 85° C. for 2.5 hours and concentrated to dryness under reduced pressure. The residue is extracted with 30 ml. of hot water of 80° C. and filtered. The filtrate is run onto a column (3 cm diameter × 15 cm) of Amberlite XAD-2 (about 200 mesh).

The column is washed with water and subjected to a gradient elution with 300 ml. of water and 300 ml. of 100% ethanol. The object compound emerges in the 130 ml.- to 220 ml.-fractions, which are pooled and concentrated under reduced pressure to evaporate the ethanol. The residue is run onto a column (2 cm diameter × 30 cm) of carboxymethyl-cellulose. The column is subjected to a gradient elution with ammonium acetate of from 0.005 to 0.2M (pH 6.8). The object compound emerges in 350 ml.- to 500 ml.-fractions, which are pooled and lyophilized to yield fluffy powder. Yield 112 mg.

$[\alpha]_D^{24}$ = −44.3° (c=0.53, in 5% acetic acid), Rf$^1$=0.088, Rf$^2$=0.73.

Amino acid analysis: His, 0.96; Arg, 1.04; Trp, 0.92; Ser, 0.96; Glu 0.99; Pro, 1.08; Ala 1.00; Leu, 1.00; Phe, 1.00; ethylamine 1.04 (85% recovery).

(II) In a mixture of 1 ml. of glacial acetic acid and 20 ml. of methanol dissolved 100 mg. of the compound which is produced by the procedure of the above (b), followed by the addition of 100 mg. of palladium black. The mixture is subjected to a catalytic reduction under atmospheric pressure for 2 days and subjected to filtration to remove the catalyst. The filtrate is concentrated to dryness under reduced pressure. The residue is dissolved in 3 ml. of 0.005M aqueous solution of ammonium acetate. The solution is run onto a column (2 cm diameter × 30 cm) of carboxymethyl-cellulose and the column is subjected to a gradient elution under the same condition as in the above procedure (I). 350 ml.- to 460 -ml. fractions are pooled and lyophilized to yield the object compound, whose Rf value and specific rotation are identical with those of the compound produced in the above (I).

(III) In 5 ml. of anhydrous hydrogen fluoride containing 0.2 ml. of anisole and 0.1 ml. of mercaptoethanol are dissolved the compound which is produced by the procedure as in the above (b) and the mixture is stirred at 0° C. for 40 minutes. The mixture is concentrated to dryness under reduced pressure to evaporate the hydrogen fluoride. The residue is dissolved in 10 ml. of water and the insolubles are removed by filtration with Celite ® (Registered trade name of the product produced by Johns-Manville, U.S.A.). The filtrate is passed through a column (1 cm diameter × 10 cm) of Amberlite CG-410 (acetate form) and the column is washed with water. The effluent and the washings are combined and run onto a column (2 cm diameter × 30 cm). The column is subjected to a gradient elution under the same condition as in the above (I). 340 ml.- to 460 ml.-fractions are pooled and lyophilized to yield the object compoud. Yield 42 mg.

The compound which is produced just above is identical in Rf value, specific rotation and $ED_{50}$ value of ovulation inducing activity with the compound which is produced by the process of the above (I).

EXAMPLE 6

Production of
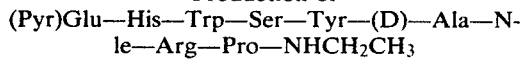
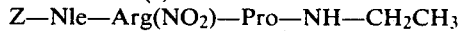

(a) Production of
Z—Nle—Arg($NO_2$)—Pro—NH—$CH_2CH_3$

In 4 ml. of 25% solution of hydrogen bromide in glacial acetic acid is dissolved 477.5 mg. of Z—Arg-($NO_2$)—Pro—NH—$CH_2CH_3$ and the solution is stirred at room temperature for 30 minutes, followed by the addition of dry ether. The resultant precipitates are collected by filtration, washed with ether and dried over sodium hydroxide under reduced pressure.

On the other hand, 265.3 mg. of Z—Nle—OH is dissolved in a mixture of 2 ml. each of ethyl acetate and dioxane. While the solution is cooled to 0° C., 187 mg. of HONB and 226 mg. of DCC are added to the solution and the mixture is stirred for 3 hours.

The urea compound which is separated is removed by filtration. The filtrate is added to a solution of the above produced precipitates in 1 ml. of dimethylformamide, followed by the dropwise addition of 0.28 ml. of triethylamine. The mixture is stirred for 12 hours and subjected to distillation to evaporate the solvent. The residue is extracted with 100 ml. of chloroform. The extract is washed with 5% aqueous solution of sodium bicarbonate, water, 0.5N hydrochloric acid and water in this order and dried over anhydrous sodium sulfate. The chloroform is evaporated by distillation. The residue is triturated with ether and reprecipitated from ethanol with ether to yield the object compound. Yield 410 mg. Melting at 109°–111° C. (decomposition), $[\alpha]_D^{22} = -50.4°$ (c = 0.5, ethanol).

Elemental analysis, (for $C_{27}H_{42}O_7N_8 \cdot \frac{1}{2}H_2O$): Calcd.: C, 54.07; H, 7.22; N, 18.68. Found: C, 53.79; H, 7.09; N, 18.24.

(b) Production of
Z—(D)—Ala—Nle—Arg($NO_2$)—Pro—NH—$CH_2CH_3$

In 5 ml. of 25% solution of hydrogen bromide in glacial acetic acid is dissolved 200 mg. of Z—Nle—Arg($NO_2$)—Pro—NH—$CH_2CH_3$ and the solution is stirred at room temperature for 40 minutes, followed by the addition of 50 ml. of dry ether. The resultant precipitates are collected by filtration, washed with ether and dried. The precipitates are run onto a column (1 cm diameter × 5 cm) of Amberlite IRA-410 (free form) with 40% aqueous methanol as developer to remove the hydrogen bromide. The methanol is evaporated from the effluent by distillation and the residue is lyophilized to yield 120 mg. of powder. In a mixture of 20 ml. of dichloromethane and 5 ml. of dimethylformamide are dissolved the powder produced just above and 44.7 mg. of Z—(D)—Ala—OH. While cooling the solution to 0° C., 40 mg. of HONB and 46 mg. of DCC are added. The mixture is stirred at room temperature for 12 hours. The dicyclohexylurea which separates is removed by filtration and the filtrate is concentrated to dryness under reduced pressure. The residue is dissolved in 120 ml. of ethyl acetate. The solution is washed with 4% aqueous solution of sodium bicarbonate and water, and dried over anhydrous sodium sulfate and is concentrated to dryness under reduced pressure. The residue is dissolved in a little amount of ethanol and precipitated with ether and such precipitation is repeated to yield the object compound as powder. Yield 132 mg. $[\alpha]_D^{26} = -48.5°$ (c = 0.5, methanol).

Elemental analysis, (for $C_{30}H_{47}O_8N_9$): Calcd.: C, 54.45; H, 7.16; N, 19.05. Found: C, 54.48; H, 7.23; N, 18.72.

$Rf^1 = 0.79$, $Rf^2 = 0.92$, $Rf^4 = 0.66$.

(c) Production of
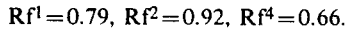
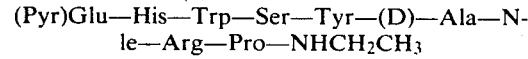

In 5 ml. of 25% solution of hydrogen bromide in glacial acetic acid is dissolved 100 mg. of Z—(D-)—Ala—Nle—Arg($NO_2$)—Pro—NH—$CH_2CH_3$ and the solution is stirred at room temperature for 50 minutes, followed by the addition of 40 ml. of dry ether. The resultant precipitates are collected by filtration, washed with ether and dried over sodium hydroxide under reduced pressure. The product is run onto a column of Amberlite CG-45 (free form) with 40% aqueous methanol to remove the hydrogen bromide. The methanol is removed from the effluent by distillation under reduced pressure and the residue is lyophilized. The lyophilizate and 100 mg. of (Pyr)Glu—His—Trp—Ser—Tyr—OH are dissolved in 4 ml. of dimethylformamide. After the addition of 45 mg. of HONB, the mixture is cooled to −5° to −7° C., followed by the addition of 40 mg. of DCC. The mixture is stirred under cooling with ice for 5 hours and at room temperature for 10 hours. The dimethylformamide is removed by evaporation and 30 ml. of ethyl aetate is added to the residue. The mixture is filtered and the filter cake is dried. The product is dissolved in 2 ml. of anhydrous hydrogen fluoride containing 0.05 ml. of anisole and 0.05 ml. of mercaptoethanol and the solution is stirred at 0° C. for 40 minutes. The hydrogen fluoride is removed by distillation under reduced pressure and the residue is dissolved in 10 ml. of water. The insolubles are removed by filtration and the filtrate is run onto a column (1 cm diameter × 5 cm) of Amberlite IRA-410 (acetate form), whereby the product is converted to the acetate. The effluent is passed through a column (1.5 cm diameter × 30 cm) of carboxymethylcellulose and the column is subjected to a gradient elution with 400 ml. of 0.005M ammonium acetate and 400 ml. of 0.2M ammonium acetate. 290 ml.- to 320 ml.-fractions which show the maximum absorption in the ultraviolet absorption spectrum are pooled and lyophilized to yield fluffy powder. Yield 105 mg. $Rf^1=0.063$, $Rf^2=0.360$, $[\alpha]_D^{26}=-46.0°$ (c=0.3, 5% aqueous acetic acid).

Amino acid analysis (hydrolysis with 5.7N hydrochloric acid in the presence of thioglycolic acid).

Glu, 1.10; His, 1.02; Trp. 0.91; Ser, 0.98; Tyr, 1.00; Ala, 1.00; Nle, 1.02; Arg, 0.98; Pro, 0.97; ethylamine 1.04 (84% recovery)

EXAMPLE 7

Production of (Pyr)Glu—His—Trp—Ser—Phe—(D-)—Ala—Ile—Arg—Pro—NHCH$_2$CH$_3$

3 G. of BOC—Pro—resin (proline content: 0.314 millimol/g) is supplied to a reactor of peptide automatic synthesizer (APS-800 made by Shimidzu Seisakusho, Ltd., Japan) and swelled with dichloromethane for 12 hours and amino acids are introduced in the following cycle.

Dichloromethane (3 minutes×3 times)→50% trifluoroacetic acid/dichloromethane (10 minutes and 30 minutes, 2 times)→dichloromethane (3 minutes×3 times)→ethanol (3 minutes×3 times)→dichloromethane (3 minutes×3 times)→10% triethylamine/chloroform (10 minutes)→chloroform (3 minutes×3 times)→dichloromethane (3 minutes×2 times)→BOC-amino acid→anhydride (produced by conventional method from BOC-amino acid and DCC) (30 minutes and 60 minutes, 2 times)→acetylation (dichloromethane, triethylamine and acetic anhydride) (1 hour) dichloromethane (3 minutes×3 times) [Only (Pyr)—Glu—OH is used as it is without BOC-group and the condensation reaction is carried out in dimethylformamide with DCC].

Finally the resin is washed with ethanol, chloroform, dimethylformamide and ether in the order mentioned, and dried. Yield 4.12 g. The following BOC-amino acids are employed.

BOC—Arg(Tos), BOC—Ile, BOC—(D)—Ala, BOC—Phe, BOC—Ser (Bzl), BOC—Trp, BOC—His(-Tos).

3 Grams of the resin which is produced as above is suspended in 20 ml. of dimethylformamide and the solution is saturated with ethylamine at 20° C. The mixture is stirred at room temperature for 40 hours. The resin is removed by filtration and the filtrate is concentrated to dryness under reduced pressure. The residue is triturated with ether to yield powder of crude (Pyr)-Glu—His(Tos)—Trp—Ser(Bzl)—Phe—(D-)—Ala—Ile—Arg(Tos)—Pro—NH—CH$_2$CH$_3$. Yield 720 mg. The powder is dissolved in a mixture of ethyl acetate, pyridine, acetic acid and water (60:20:6:10) and the solution is run onto a column (3 cm diameter×20 cm) of silica gel which is prepared with the same kind of the solvent mixture. The column is eluted with the same kind of the solvent mixture. Fractions showing Rf value of 0.4 on thin layer chromatography on silica gel with methanol-chloroform (15:85) are pooled and concentrated to dryness under reduced pressure. The residue is triturated with ethyl acetate and the resultant powder is collected by filtration. Yield 240 mg. The powder is dissolved in 5 ml. of hydrogen fluoride containing 0.05 ml. of thioglycolic acid and 0.2 ml. of anisole and the solution is stirred at 0° C. for one hour. The hydrogen fluoride is removed by evaporation and the residue is dissolved in 10 ml. of water. The solution is run onto a column (1 cm diameter×10 cm) of Amberlite IRA-410 (acetate form). The effluent is purified by passing through a column (2 cm diameter×10 cm) of Amberlite XAD-2 twice, a column (1.9 cm diameter×25 cm) of carboxymethyl-cellulose twice and a column (1 cm diameter×60 cm) of Cephadex LH-20 once, and finally lyophilized to yield fluffy powder. Yield 42 mg. $Rf^1=0.071$, $Rf^2=0.37$.

Amino acid analysis (hydrolysis with hydrochloric acid in the presence of thioglycolic acid)

Glu, 1.01; His, 0.93; Trp, 0.92; Ser, 0.99; Phe, 1.00; Ala, 1.03; Ile, 0.98; Arg, 1.00; Pro, 1.08; ethylamine 1.04 (88% recovery)

EXAMPLE 8

Production of (Pry)Glu—Tyr—Trp—Ser—Tyr—(D-)—Ala—Leu—Arg—Pro—NHCH$_2$CH$_3$ (a) Preparation of BOC—Tyr—(OBzl)—(D)—Ala—OBzl In 100 ml. of acetonitrile are dissolved 11.1 g. of BOC—Tyr—(OBzl)—OH and 10.9 g. of (D)—Ala—OBzl-p-toluene-sulfonate. The solution is cooled to 0° C. and 6.8 g. of DCC, 4.5 g. of HONB and 4.34 ml. of triethylamine are added. The mixture is stirred at room temperature for 19 hours, after which the precipitated urea compound is filtered off. The filtrate is distilled and the residue is extracted with 200 ml. of ethyl acetate. The extract is washed with a 5% aqueous solution of sodium hydrogen carbonate, 0.1N hydrochloric acid and water in the order mentioned and dried over Na$_2$SO$_4$. The ethyl acetate is distilled off and the residue is crystallized from petroleum ether and, then, recrystallized from ethyl acetate-petroleum ether. Yield 13.5 g. Melting point: 113°–114° C.; $[\alpha]_D^{21}=+18.4°$ (c=1, methanol), $Rf^4=0.76$.

Elemental analysis, for C$_{31}$H$_{36}$O$_6$N$_2$: Calcd.: C, 69.90; H, 6.81; N, 5.26%. Found: C, 69.72; H, 6.75; N, 5.42%.

(b) Preparation of BOC—Ser—Tyr—(OBzl)—(D)—Ala—OBzl

In 100 ml. of trifluoroacetic acid is dissolved 11 g. of BOC—Tyr(OBzl)—(D)—Ala—OBzl. The solution is allowed to stand at room temperature for 30 minutes, after which time the solvent is distilled off under reduced pressure.

The residue is dried over sodium hydroxide under reduced pressure in a desiccator.

On the other hand, 4.1 g. of BOC—Ser and 4.0 g. of 2,4-dinitrophenol are dissolved in 50 ml. of tetrahydrofuran. This solution is cooled to 0° C. and, after the addition of 4.5 g. of DCC, stirred at 0° C. for 2 hours.

The precipitated dicyclohexylurea is filtered off, and the amine component (H—Tyr(OBzl)—(D-)—Ala—OBzl) previously prepared is dissolved in the filtrate. The solution is cooled to 0° C. and 4.2 ml. of triethylamine is added dropwise. The solution is stirred at room temperature for 5 hours, after which the tetrahydrofuran is distilled off under reduced pressure.

The residue is dissolved in 200 ml. of ethyl acetate and the solution is washed with a 5% aqueous solution of sodium hydrogen carbonate, 0.1N hydrochloric acid and water in the order mentioned, followed by drying over Na$_2$SO$_4$. The ethyl acetate is distilled off and the residue is crystallized from petroleum ether and, then, recrystallized from ethyl acetate-petroleum ether. Yield 9.7 g.

Rf⁴=0.57; $[\alpha]_D^{21}$= −4.1° (c=1, methanol); Melting point: 124°–125° C.

Elemental analysis, for $C_{34}H_{41}O_8N_3$: Calcd.: C, 65.89; H, 6.67; N, 6.78%. Found: C, 65.82; H, 6.59; N, 6.50%.

(c) Preparation of BOC—Ser—Tyr—(D)—Ala—Leu—Arg(NO₂)—Pro—NHCH₂CH₃

In 100 ml. of methanol is dissolved 2.16 g. of BOC—Ser—Tyr(OBzl)—(D)—Ala—OBzl and, in the presence of palladium black, catalytic reduction is carried out for 4 hours, after which time the catalyst is filtered off. The methanol is distilled off and the residue is dissolved in 10 ml. of dimethylformamide. In this solution are dissolved 1.6 g. of H—Leu—Arg(NO₂)—Pro—NHCH₂CH₃ and 690 mg. of HONB. After the solution is cooled to 0° C., 795 mg. of DCC is added with stirring. The mixture is stirred at 0° C. for 2 hours and, then, at room temperature for 5 hours. The precipitated urea compound is filtered off and the dimethylformamide is removed by distillation under reduced pressure. The residue is extracted with 50 ml. of n-butanol and washed with a 5% aqueous solution of sodium hydrogen carbonate, 0.1N hydrochloric acid and water in the order mentioned. The n-butanol is distilled off and the residue is solidified with ether and precipitated from ethanol-ether. Yield 2.25 g. Rf⁴=0.30; Melting point: 149°–151° C. (decomp.); $[\alpha]_D^{27}$= −26.6° (c=1, methanol).

Elemental analysis, for $C_{39}H_{63}O_{12}N_{11}\cdot3/2H_2O$: Calcd.: C, 51.75; H, 7.35; N, 17.02%. Found: C, 51.89; H, 7.30; N, 16.72%.

(d) Preparation of Z—Tyr(Z)—Trp—OBzl

In a solvent mixture of dioxane-ethyl acetate (50 ml.-10 ml.) are dissolved 9.0 g. of Z—Tyr—(Z)—OH and 10.2 g. of Trp—OBzl-p-toluenesulfonate. The solution is cooled to 0° C. and 3.93 g. of HONB, 4.53 g. of DCC and 3.0 ml. of triethylamine are added. The mixture is stirred for 5 hours, after which the precipitated urea compound is filtered off. The solvent is removed by distillation under reduced pressure and the residue is extracted with 200 ml. of ethyl acetate. The extract is washed with a 5% aqueous solution of sodium hydrogen carbonate, 1N hydrochloric acid and water in the order mentioned, followed by drying over Na₂SO₄. The ethyl acetate is distilled off and the residue is crystallized from petroleum ether and recrystallized from ethyl acetate-petroleum ether. Yield 13 g. Rf⁴=0.88; Melting point: 103°–104° C.; $[\alpha]_D^{23}$= −4.7° (c=1, methanol).

Elemental analysis, for $C_{43}H_{39}O_8N_3$: Calcd.: C, 71.16; H, 5.42; N, 5.79%. Found: C, 71.11; H, 5.29; N, 5.76%.

(e) Preparation of Z—(Pyr)Glu—Tyr—Trp

In 100 ml. of methanol is dissolved 5.8 g. of Z—Try(Z)Trp—OBzl and, in the presence of palladium black, catalytic reduction is carried out for 5 hours. After the catalyst is filtered off, the methanol is removed by distillation under reduced pressure. The residue is dissolved in 20 ml. of dimethylformamide, and 3.39 g. of Z—(Pyr)Glu—ONB and 1.12 ml. of triethylamine are added. The mixture is stirred at room temperature for 12 hours, after which the dimethylformamide is distilled off. To the residue are added 100 ml. of ethyl acetate and 100 ml. of water. The water layer is rendered acidic with 1N hydrochloric acid and extracted with 100 ml. of n-butanol. The extract is washed with water and the n-butanol is distilled off. The residue is triturated with ether to yield powder. This is reprecipitated from ethanol-ether. Yield 4.5 g. Rf¹=0.63; Melting point: 165°–169° C. (decomp.); $[\alpha]_D^{21}$= −4.8° (c=0.5 in methanol).

Elemental analysis, for $C_{33}H_{32}O_8N_4\cdot H_2O$: Calcd.: C, 62.85; H, 5.43; N, 8.89%. Found: C, 62.96; H, 5.35; N, 8.76%.

(f) Preparation of (Pyr)Glu—Tyr—Trp—Ser—Tyr—(D)—Ala—Leu—Arg—Pro—NHCH₂CH₃

In 20 ml. of methanol is dissolved 184 mg. of Z—(Pyr)Glu—Tyr—Trp and, in the presence of palladium black, hydrogenation is carried out for 3 hours. After the catalyst has been filtered off, the methanol is distilled off under reduced pressure and the residue is dissolved in 2 ml. of dimethylformamide. On the other hand, 316 mg. of BOC—Ser—Tyr—(D)—Ala—Leu—Arg(NO₂)—Pro—NHCH₂CH₃ is treated with 10 ml. of trifluoroacetic acid in the presence of 0.36 ml. of 1N hydrochloric acid for 40 minutes. The trifluoroacetic acid is distilled off and the residue is triturated with ether and thoroughly dried over sodium hydroxide in a desiccator. This powder and 81 mg. of HONB are dissolved in the previously prepared dimethylformamide solution, followed by cooling to −2° C. Then, 93 mg. of DCC and 0.05 ml. of N-ethylmorpholine are added and the resultant mixture is stirred at 0° C. for 2 hours and, then, at room temperature overnight. The precipitated urea compound is filtered off and 50 ml. of ether is added to the filtrate. The precipitate is recovered by filtration. Yield 350 mg. This product is passed over 7 g. of silica gel using the developer solvent mixture of Rf¹. The fractions rich in the desired compound are pooled and the solvent is distilled off. The residue is triturated with ethyl acetate. Yield 270 mg. A 150 mg. portion of this product is treated with 4 ml. of anhydrous hydrogen fluoride in the presence of 0.1 ml. of anisole and 0.1 ml. of 2-mercaptoethanol at 0° C. for 1 hour, after which the hydrogen fluoride is distilled off under reduced pressure. The residue is dried over sodium hydroxide in a desiccator. The residue is extracted with 50 ml. of water and the extract is run onto a column (1 cm diameter×5 cm) of Amberlite IRA-410 (acetate form). The effluent and aqueous washings are pooled and run onto a column (1.5 cm diameter×19 cm) of carboxymethyl-cellulose. Elution is carried out by the linear gradient method using 0.005N ammonium acetate (280 ml.) to 0.15N ammonium acetate (280 ml.). The 110 ml.- to 210 ml.-fractions are pooled and lyophilized to obtain 95 mg. of the contemplated product. Rf¹=0.35; $[\alpha]_D^{24}$= −39.0° (c=0.5, 5% acetic acid); amino acid analysis (hydrolysis with 5.7N HCl in the presence of 4% thioglycolic acid at 110° C.); Arg, 1.07; Trp, 1.03; Ser, 0.89; Glu, 1.00; Pro, 1.00; Ala, 1.00; Leu, 1.00; Tyr, 2.00; ethylamine, 1.05. (81% recovery).

EXAMPLE 9

Production of (Pyr)Glu—p—NH₂—Phe—Trp—Ser—Tyr—(D)—Ala—Leu—Arg—Pro—NH—CH₂—CH₃

(a) Preparation of BOC—p—NO₂—Phe—OH

In a mixture of 40 ml. of 1N aqueous solution of sodium hydroxide and 150 ml. of dimethylformamide are dissolved 6.3 g. of p—NO₂—Phe—OH and 13.3 g. of t-butylpentachlorophenyl carbonate. Following the addition of 5 ml. of triethylamine, the solution is reacted at room temperature for 48 hours. The solvent is distilled off and the residue is dissolved in water, followed by extraction with ether. The water layer is adjusted to pH 3 with citric acid and extracted with ethyl acetate. The organic layer is dried over anhydrous magnesium sulfate and the solvent is distilled off. The residue is triturated with petroleum ether and recovered by filtration. The product is purified by column chromatography on silica gel and the fractions containing the desired product is pooled and distilled to remove the solvent. The residue is crystallized from ether-petroleum ether. Yield 3.8 g. Melting point: 103°–104° C.; $[\alpha]_D^{24} = -32.0°$ (c=0.75, dimethylformamide); $Rf^4 = 0.61$.

Elemental analysis, (for $C_{14}H_{18}O_6N_2$): Calcd.: C, 54.19; H, 5.85; N, 9.03%. Found: C, 54.21; H, 5.86; N, 9.21%.

(b) Preparation of BOC—p—NH₂—Phe—OH

In 80 ml. of methanol is dissolved 2.0 g. of BOC—p—NO₂—Phe—OH and, using palladium black as the catalyst, catalytic reduction is carried out at room temperature for 8 hours. The catalyst is removed by filtration and the solvent is distilled off. The residue is triturated with petroleum ether and recovered by filtration. The product is further recrystallized from ethyl acetate-petroleum ether. Yield 1.5 g. Melting point: 121° C.; $[\alpha]_D^{24} = -2.2°$ (c=1.0, dimethylformamide); $Rf^4 = 0.40$.

Elemental analysis, (for $C_{14}H_{20}O_4N_2$): Calcd.: C, 59.98; H, 7.19; N, 9.99%. Found: C, 59.47; H, 7.20; N, 9.71%.

(c) Preparation of BOC—p—NH—Z—Phe

In 20 ml. of a 1N aqueous solution of sodium hydrogen carbonate is dissolved 1.5 g. of BOC—p—NH₂—Phe—OH. With vigorous stirring under cooling with ice, 1.1 g. of benzyloxycarbonyl chloride is added. In the course of reaction 30 ml. of water is further added and the reaction is conducted for 3 hours. Thereafter, 1N hydrochloric acid is added to the reaction mixture to adjust the pH to 2 and the resultant oily precipitate is extracted with ethyl acetate. The ethyl acetate layer is collected, washed with water and dried over anhydrous magnesium sulfate. The solvent is distilled off and the residue is triturated with petroleum ether to obtain a crude product. This product is recrystallized from ether-petroleum ether. Yield 1.84 g.; Melting point: 156°–157° C.; $[\alpha]_D^{24} = -3.34°$ (c=0.7, dimethylformamide); $Rf^4 = 0.67$.

Elemental analysis, (for $C_{22}H_{26}O_6N_2$): Calcd.: C, 63.75; H, 6.32; N, 6.76%. Found: C, 63.76; H, 6.25; N, 6.86%.

(d) Preparation of
BOC—Trp—Ser—Tyr—(D)—Ala—Leu—Arg(NO₂)—Pro—NH—CH₂—CH₃

In 5 ml. of dimethylformamide is dissolved 466 mg. of H—Ser—Tyr—(D)—Ala—Leu—Arg(NO₂)—Pro—NH—CH₂—CH₃. Following the addition of 370 mg. of BOC—Trp—ONB, the solution is reacted at room temperature for 3 hours. The solvent is distilled off and ethyl acetate is added to the residue. The resultant powder is recovered by filtration and boiled in ethyl acetate, followed by cooling and allowing it to stand. The precipitate is collected by filtration. Yield 590 mg. Melting point: 189°–190° C. (decomposition): $[\alpha]_D^{22} = -43.8°$ (c=0.6, dimethylformamide); $Rf^4 = 0.32$.

Elemental analysis, (for $C_{50}H_{73}O_{13}N_{13}·2H_2O$): Calcd.: C, 54.58; H, 7.06; N, 16.55%. Found: C, 54.84; H, 6.90; N, 16.54%.

(e) Preparation of

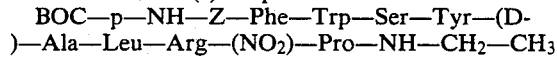

In the presence of mercaptoethanol, 560 mg. of BOC—Trp—Ser—Tyr—(D)—Ala—Leu—Arg(NO₂)—Pro—NH—CH₂—CH₃ is treated with 5 ml. of trifluoroacetic acid at room temperature for 30 minutes, after which time ether is added. The resultant precipitate is recovered by filtration and dried over sodium hydroxide in a desiccator.

The product is dissolved in 5 ml. of dimethylformamide and the solution is neutralized with 0.1 ml. of N-ethylmorpholine.

To this solution is added a dimethylformamide solution of BOC—p—NH—Z—Phe—ONB which has been prepared from 217 mg. of BOC—p—NH—Z—Phe and 145 mg. of HONB by the DCC process. The mixture is reacted at room temperature for 12 hours, after which time the solvent is distilled off. To the residue is added ethyl acetate and the resultant solid is recovered by filtration. Yield 518 mg. Melting point: 119°–120° C. (decomposition); $[\alpha]_D^{22} = -29.7°$ (c=0.6, dimethylformamide); $Rf^4 = 0.37$.

Elemental analysis, (for $C_{67}H_{89}O_{15}N_{15}·2H_2O$): Calcd.: C, 58.29; H, 6.65; N, 15.22%. Found: C, 58.18; H, 6.69; N, 14.81%.

(f) Preparation of

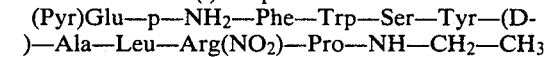

In the presence of mercaptoethanol, 470 mg. of BOC—p—NH₂—Z—Phe—Trp—Ser—Tyr—(D)—Ala—Leu—Arg(NO₂)—Pro—NH—CH₂—CH₃ is treated at room temperature for 30 minutes, after which ether is added. The resultnt precipitate is recovered by filtration and dried over sodium hydroxide in a desiccator. The product is dissolved in 6 ml. of dimethylformamide and the solution is neutralized with 0.045 ml. of N-ethylmorpholine. Following the addition of 185 mg. of IBOC—(Pyr)—Glu—OSu, the solution is reacted at room temperature for 48 hours. The solvent is distilled off and the residue is triturated with ethyl acetate. The resultant powder is recovered by filtration. The described procedure gives 425 mg. of

A 375 mg. portion of this product is treated with 5 ml. of anhydrous hydrogen fluoride in the presence of mercaptoethanol and anisole at 0° C. for 1 hour. After removal of the hydrogen fluoride by distillation, the residue is dissolved in water and extracted with ether. The water solution is passed columnwise over Amberlite IR-410 (acetate form, 0.9 cm diameter × 15 cm) and the effluent and aqueous washings are pooled and lyophilized. The product is dissolved in 0.005M ammonium acetate buffer and run onto a column (1.8 cm. diameter×19 cm) of carboxymethyl-cellulose. Elution is carried out by the linear gradient method using 0.005M (300 ml.) to 0.2M (300 ml.) ammonium acetate buffer and the 90 ml.- to 140 ml.-fractions are pooled and lyophilized. Yield 170 mg.

$[\alpha]_D^{22} = -41.8°$ (c=0.56, 5% acetic acid); $Rf^1 = 0.16$.
Elemental analysis, (for $C_{58}H_{78}O_{12}N_{15}.3CH_3COOH.4H_2O$): Calcd.: C, 53.77; H, 6.91; N, 14.70%. Found: C, 54.09; H, 6.58; N, 14.84%.

Amino acid analysis (hydrolysis with 5.7N hydrochloric acid in the presence of 4% thioglycolic acid at 110° C. for 24 hours):

Arg, 0.97; Trp, 0.84; p—$NH_2$—Phe, 0.97; Ser, 1.00; Glu, 1.00; Pro, 0.99; Ala, 1.02; Leu, 1.02; Tyr, 1.08; ethylamine, 1.00.

EXAMPLE 10

Production of
(Pyr)Glu—Trp—Trp—Ser—Tyr—(D-)—Ala—Leu—Arg—Pro—NH—$CH_2CH_3$ (a) Preparation of Z—(Pyr)Glu—Trp—OBzl To a solution of Z—(Pyr)Glu—ONB (1.7 g) and H—trp—OBzl p-toluenesulfonate (2.1 g) in acetonitrile (50 ml) was added triethylamine (0.61 ml), and the mixture is stirred for 12 hours at room temperature. The reaction mixture is evaporated in vacuo to dryness. The residue is dissolved in ethyl acetate (100 ml), washed with 1N HCl and 5% aqueous $NaHCO_3$, dried over anhydrous $Na_2SO_4$ and evaporated to dryness. The residue is crystallized from petroleum ether and recrystallized from ethyl acetate-petroleum ether: yield 1.7 g; melting point 129°-130° C.; $[\alpha]_D^{25} = +3.1°$ (c=1.0 in dimethylformamide); $Rf^4 = 0.42$.

Elemental analysis, for $C_{31}H_{29}O_6N_3$: Calcd.: C, 69.00; H, 5.42; N, 7.79%. Found: C, 68.85; H, 5.48; N, 7.53%.

(b) Preparation of
BOC—Trp—Ser—Tyr—(D)—Ala—Leu—Arg($NO_2$)—Pro—NH—$CH_2CH_3$

BOC—Ser—Tyr—(D)—Ala—Leu—Arg($NO_2$)—Pro—NH—$CH_2CH_3$ (670 mg) is treated with trifluoroacetic acid (10 ml) at room temperature for 20 minutes, and to this solution is added dry ether (50 ml) to yield a fine solid which is dried over NaOH-pellets in vacuo. The resulting powder is dissolved in dimethylformamide (5 ml) and to this solution is added triethylamine (0.11 ml) together with BOC—Trp—ONB which is prepared from BOC—Trp—OH (243 mg) and HONB (150 mg) by the DCC method. The mixture is stirred for 12 hours at room temperature and the resulting product is precipitated by addition of ethyl acetate (50 ml). The precipitate is collected by filtration and washed with water. The resulting precipitate is purified by reprecipitation from dimethylformamide-ethyl acetate: yield 720 mg; melting point 190°-193° C.; $[\alpha]_D^{25} = -42.4°$ (c=0.5 in dimethylformamide); $Rf^4 = 0.27$.

Elemental analysis, for $C_{50}H_{73}O_{13}N_{13}H_2O$: Calcd.: C, 55.49; H, 6.98; N, 16.82%. Found: C, 55.14; H, 7.16; N, 16.76%.

(c) Preparation of
(Pyr)Glu—Trp—Trp—Ser—Tyr—(D-)—Ala—Leu—Arg—Pro—NH—$CH_2CH_3$

Z—(Pyr)Glu—Trp—OBzl obtained above (215 mg) is dissolved in methanol (50 ml) and then hydrogenated over palladium-black as a catalyst for 3 hours. The solution is filtered to remove the catalyst and evaporated to dryness. The residue is washed with ether and collected by filtration to give the corresponding free acid.

BOC—Trp—Ser—Tyr—(D)—Ala—Leu—Arg—($NO_2$)—Pro—NH—$CH_2CH_3$ (426 mg) is treated with trifluoroacetic acid (5 ml) in the presence of 2-mercaptoethanol (0.1 ml) and N—HCL (0.4 ml) at room temperature for 30 minutes, and to this solution is added dry ether to give a fine white solid which is collected by filtration and dried over NaOH-pellets in vacuo to give the corresponding free base.

The powder obtained is dissolved in dimethylformamide (2 ml) together with N-ethylmorpholine (0.06 ml), and to this are added the above described free acid and HONB (102 mg). The mixture is cooled to 0° C. and to this is added DCC (110 mg). The solution is stirred for 2 hours at 0° and for additional 10 hours at room temperature. The reaction mixture is filtered to remove the formed dicyclohexylurea and the filtrate is diluted with ethyl acetate to give a fine solid which is collected by filtration to give the crude product. The resulting crude protected nonapeptide ethylamide is purified by a column of silica gel (solvent system, ethyl acetate:-Pyridine:acetic acid:$H_2O$, 60:20:6:10). The fractions which contain the pure product (checked by thin layer chromatography) were combined and evaporated to give the solid. The solid (250 mg) is treated with 5 ml of hydrogen fluoride in the presence of anisole (0.1 ml).and 2-mercaptoethanol (0.1 ml) at 0° C. for 60 minutes and the hydrogen fluoride is removed in vacuo. The residue is dissolved in 20 ml of water and passed through a column of Amberlite CG-140 (acetate form, 1×10 cm) and the column is washed well with water. The eluate and washings are combined and subjected to a chromatography on a carboxymethylcellulose column (1.2 diameter×30 cm) with a gradient elution method (pH 6.8, ammonium acetate buffer, 0.005M/0.15M=300 ml/300 ml). The pure peptide is eluated in 160-260 ml fractions which are combined and lyophilized to a constant weight: yield 100 mg; $[\alpha]_D^{25} = -47.2°$ (c=0.25 in 5% acetic acid).

$Rf^1 = 0.31$, $Rf^2 = 0.76$. Amino acid analysis: His, 0.96; Arg, 1.01; Trp, 1.89; Glu, 0.92; Ser, 0.96; Pro, 1.11; Ala, 1.00; Leu, 1.02; Tyr, 1.05 (86% recovery).

What is claimed:

1. A compound of the formula (Pyr)Glu—$R_1$—Trp—Ser—$R_2$—(D)—Ala—$R_3$—Arg—Pro—NH—$R_4$ wherein $R_1$ is His, Tyr, or p—$NH_2$—Phe, $R_2$ is Tyr or Phe, $R_3$ is Leu, Ile or Nle and $R_4$ is alkyl of 1 to 3 carbon atoms which may be substituted therefor, by hydroxy.

2. A compound as claimed in claim 1, wherein $R_1$ is His.

3. The compound as claimed in claim 1, wherein $R_1$ is Tyr or p—$NH_2$—Phe.

4. The compound as claimed in claim 1, wherein $R_2$ is Tyr.

5. A compound as claimed in claim 1, wherein $R_3$ is Leu.

6. The compound as claimed in claim 1, wherein $R_1$ is His, $R_2$ is Tyr, $R_3$ is Leu and $R_4$ is ethyl.

7. The compound as claimed in claim 1, wherein $R_1$ is His, $R_2$ is Tyr, $R_3$ is Leu and $R_4$ is n-propyl.

8. The compound as claimed in claim 1, wherein $R_1$ is His, $R_2$ is Tyr, $R_3$ is Leu and $R_4$ is 2-hydroxyethyl.

9. The compound as claimed in claim 1, wherein $R_1$ is His, $R_2$ is Tyr, $R_3$ is Leu and $R_4$ is i-propyl.

10. The compound as claimed in claim 1, wherein $R_1$ is His, $R_2$ is Phe, $R_3$ is Leu and $R_4$ is ethyl.

11. The compound as claimed in claim 1, wherein $R_1$ is His, $R_2$ is Tyr, $R_3$ is Nle and $R_4$ is ethyl group.

12. The compound as claimed in claim 1, wherein $R_1$ is His, $R_2$ is Phe, $R_3$ is Ile and $R_4$ is ethyl group.

13. The compound as claimed in claim 1, wherein $R_1$ is Tyr, $R_2$ is Tyr, $R_3$ is Leu and $R_4$ is ethyl group.

14. The compound as claimed in claim 1, wherein $R_1$ is p—$NH_2$—Phe, $R_2$ is Tyr, $R_3$ is Leu and $R_4$ is ethyl.

15. A compound as claimed in claim 1 wherein $R_2$ is Phe.

16. A compound as claimed in claim 1 wherein $R_2$ is Tyr and $R_4$ is alkyl of 3 carbon atoms.

17. A compound as claimed in claim 1 wherein $R_2$ is Tyr, and $R_4$ is —$CH_2CH_2OH$.

18. A compound of the formula (Pyr)Glu—His—Trp—Ser—Tyr—D—Ala—Leu—Arg—Pro—X wherein X is $NHCH_2CH_3$ or $NHCH_2CH_2CH_3$.

* * * * *